(12) United States Patent
Guram et al.

(10) Patent No.: US 6,534,664 B1
(45) Date of Patent: Mar. 18, 2003

(54) CATALYST LIGANDS, CATALYTIC METAL COMPLEXES AND PROCESSES USING SAME

(75) Inventors: Anil S. Guram, Cupertino, CA (US); Anne Marie LaPointe, Santa Clara, CA (US); Howard W. Turner, Campbell, CA (US); Tetsuo Uno, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 134 days.

(21) Appl. No.: 09/680,494

(22) Filed: Oct. 5, 2000

Related U.S. Application Data

(62) Division of application No. 09/168,772, filed on Oct. 8, 1998.

(51) Int. Cl.$^7$ .............................. C07F 9/00; C07F 13/00; C07F 7/00
(52) U.S. Cl. ...................... 556/1; 556/7; 556/8; 556/12; 556/21; 556/42; 556/45; 556/51; 556/54; 549/206; 546/2; 534/15
(58) Field of Search .................................. 556/1, 42, 45, 556/51, 54, 7, 8, 12, 21; 534/15; 546/2; 549/206

(56) References Cited

U.S. PATENT DOCUMENTS

| | | | |
|---|---|---|---|
| 5,153,157 A | 10/1992 | Hlatky et al. | 502/117 |
| 5,453,140 A | 9/1995 | Kolthammer et al. | 502/155 |
| 5,599,761 A | 2/1997 | Turner | 502/152 |
| 5,776,359 A | 7/1998 | Schultz et al. | 252/62.51 |
| 5,883,204 A | 3/1999 | Spencer et al. | 526/134 |
| 5,919,983 A | 7/1999 | Rosen et al. | 568/3 |
| 5,929,181 A | 7/1999 | Makovetsky et al. | 526/171 |
| 6,057,466 A | 5/2000 | Starzewski et al. | 559/19 |
| 6,214,954 B1 | 4/2001 | Nitto et al. | 526/161 |

FOREIGN PATENT DOCUMENTS

| | | | |
|---|---|---|---|
| DE | 11 19 297 | 9/1959 | |
| EP | 0 889 061 A1 | 1/1999 | |
| EP | 0 893 454 | 1/1999 | |
| EP | 0 953 571 A1 | 11/1999 | |
| WO | WO 96/18658 | 6/1996 | C08F/4/642 |
| WO | WO 98/03521 | 1/1998 | |
| WO | WO 98/34961 | 8/1998 | |
| WO | WO 98/42644 | 10/1998 | |
| WO | WO 98/42665 | 10/1998 | |

OTHER PUBLICATIONS

Sadighi et al, "A Highly Active Palladium Catalyst System for the Arylation of Anilines," Tetrahedron Letters, NL, Elsevier Science Publishers, Amsterdam, vol. 39, No. 30, Jul. 1998, pp. 5327–5330.

Cadogan et al, Reduction of Nitro– and Nitroso–Compunds by Tetravalent Phosphorus Reagents . . . , J. Chem. Soc., Perkin Transactions 1, 1975, pp. 2376–2385.

Wolfe, et al, "An Improved Catalyst System for Aromatic Carbon–Nitrogen Bond Formation: The Possible Involvement of Bis(Phosphine) Palladium Complexes as Key Intermediates," J. Am. Chem. Soc., 1996, 118, pp. 7215–7216.

Bharucha, et al, "p–Alkoxyanilines as Antinitrosamine Agents for Bacon," J. Agric. Food Chem., 1986, 34, pp. 814–818.

Ward, et al, "Solid Phase Synthesis of Aryl Amines Via Palladium Catalyzed Amination of Resin–Bound Aromatic Bromides," Tetrahedron Letters, vol. 37, No. 39, 1996, pp. 6993–6996.

Sundberg, et al, "Acid–Promoted Aromatic Substitution Processes in Photochemical and Thermal Decompositions of Aryl Azides," J. Org. Chem., vol. 38, No. 11, 1973, pp. 2052–2057.

Prokof'ev, et al, "Tautomerism and Sterodynamics of Indophenols, Amidines, and their Derivatives and Analogs . . . " Russian Journal of General Chemistry, vol. 59, 1989, pp. 1264–1272.

Wang et al, "Neutral Nickel(II)–Based Catalysts for Ethylene Polymerization," Organometallics 17, 1998, pp. 3149–3151.

*Primary Examiner*—Porfirio Nazario-Gonzalez

(57) ABSTRACT

New ligands having a backbone comprised of NCCX can be combined with a metal or metal precursor compound or formed into a metal-ligand complex to catalyze a number of different chemical transformations, including polymerization.

37 Claims, No Drawings

CATALYST LIGANDS, CATALYTIC METAL COMPLEXES AND PROCESSES USING SAME

CROSS-REFERENCE TO RELATED APPLICATIONS

This application is a division of U.S. application Ser. No. 09/168,772, filed Oct. 8, 1998, now allowed.

FIELD OF THE INVENTION

The present invention relates to new organic compounds (e.g., ligands), their metal complexes and compositions using those compounds; the invention also relates to the field of catalysis. In particular, this invention relates to new compounds which when combined with suitable metals or metal precursor compounds provide useful catalysts for various bond-forming reactions, including polymerization, oligomerization or small molecule catalysis. This invention also relates to a method of making the ligands of this invention where the synthesis involves an aryl amination reaction. The invention also relates to combinatorial chemistry in that combinatorial techniques were used in connection with creating the ligands and testing compositions containing the ligands.

BACKGROUND OF THE INVENTION

Ancillary (or spectator) ligand-metal coordination complexes (e.g., organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations.

One example of the use of these types of ancillary ligand-metal complexes and compositions is in the field of single site polymerization or oligomerization catalysis. In connection with single site catalysis, the ancillary ligand offers opportunities to modify the electronic and/or steric environment surrounding an active metal center. This allows the ancillary ligand to create possibly different polymers or oligomers. It also allows for higher reactivity under changing process conditions.

Moreover, it is always a desire to discover new ancillary ligands, which upon coordination to a metal center or addition of a metal compound or precursor will catalyze or assist in catalysis of reactions differently from known ligand systems. This invention provides new ancillary ligands that may be used for coordination to a metal center or included in a composition with a metal or metal precursor compound. Upon coordination to the metal center or inclusion in the composition, such ligands influence the electronic and steric environment of the resulting coordination complex and may catalyze reactions differently, including more efficiently and selectively than known systems.

SUMMARY OF THE INVENTION

In one aspect, the invention disclosed herein is a new ligand, which can be characterized by the general formula:

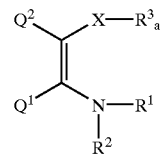

I wherein each $R^1$, $R^2$ and $R^3$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure;

$Q^1$ and $Q^2$ are, independently, selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $Q^1$ and $Q^2$ are joined together in a ring structure;

X is selected from the group consisting of O, P, S, and N atoms; and a is 1 or 2, depending on X and its oxidation state.

The ligands can be included in a composition including a suitable metal or metal precursor compound, where the composition has catalytic properties. Also, the ligands can be coordinated with a metal precursor to form metal-ligand complexes, which may be catalysts. The metal-ligand complexes of this invention may be characterized by one of the following the general formulas:

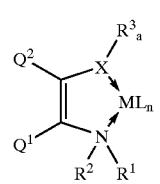

V

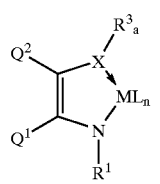

VI

VII

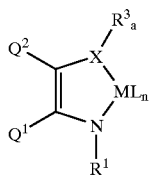

wherein $R^1$, $R^2$, $R^3$, $Q^1$, $Q^2$, and X are as defined above. In addition, M is a transition metal selected from the group consisting of Se, Y and Groups 4–12 of the Periodic Table of Elements; L is independently each occurrence, a neutral and/or charged ligand; and n is a number 0, 1, 2, 3, 4, or 5, depending on M. If X is nitrogen, a is either 1 or 2 depending on the type of bonding to the metal M. In these formulas, if X is oxygen, then a is either 0 or 1, depending on the type of bonding to the metal M. If X is phosphorus, a is either 1 or 2 depending on the type of bonding to the metal M and the oxidation state of the phosphorus. Similarly, if X is sulfur, a is 0 or 1 depending on the type of bonding to the metal M and the oxidation state of the sulfur.

These transition metal-ligand complexes or compositions catalyze reactions involving activation of and/or formation of H—Si, H—H, H—N, H—O, H—P, H—S, C—H, C—C, C=C, C≡C, C—halogen, C—N, C—O, C—S, C—P, and C—Si bonds. Specifically, such reactions include carbonylation, hydroformylation, hydroxycarbonylation, hydrocarbonylation, hydroesterification, hydrogenation, transfer hydrogenation, hydrosilylation, hydroboration, hydroamination, epoxidation, aziridination, reductive amination, C—H activation, insertion, C—H activation-insertion, C—H activation-substitution, C-halogen activation, C-halogen activation-substitution, C-halogen activation-insertion, cyclopropanation, alkene metathesis, alkyne metathesis, polymerization, alkene oligomerization, alkene polymerization, alkyne oligomerization, alkyne polymerization, co-polymerization, CO-alkene co-oligomerization, CO-alkene co-polymerization, CO-alkyne co-oligomerization and CO-alkyne co-polymerization.

Further aspects of this invention will be evident to those of skill in the art upon review of this specification.

DETAILED DESCRIPTION OF THE INVENTION

The invention disclosed herein is a new ligand that may be combined with metals or metal precursor compounds to form coordination complexes or compositions of matter, which are useful as catalysts for chemical reactions.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more carbon atoms of the alkyl is replaced by a heteroatom selected from the group consisting of N, O, P, B, S, Si, Sb, Al, Sn, As, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $—OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the $—SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the $—BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group $—PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, heteroaryl, silyl, alkoxy, aryloxy, amino and combinations thereof.

The term "amino" is used herein to refer to the group $—NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group $—SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group $—SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

In one aspect, the ligands of this invention may be characterized by the formula:

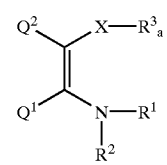

I wherein each $R^1$, $R^2$ and $R^3$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure;

$Q^1$ and $Q^2$ are, independently, selected from the group consisting of hydrogen, alkyl, substituted alkyl, cycloalkyl, substituted cycloakyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $Q^1$ and $Q^2$ are joined together in a ring structure; and X is selected from the group consisting of N, P, S and O atoms; and a is 1 or 2, depending on X.

In more specific embodiments, $R^1$ and $R^2$ are independently selected from a group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, silyl, boryl and phosphino. Specific examples of $R^1$ and $R^2$ are methyl, ethyl, propyl, butyl, cyclohexyl, cyclopropyl, cycloheptyl, t-butyl, phenyl, 2,4,6-trimethylphenyl, 2,4,6- triisopropylphenyl, 2,6-dimethylphenyl, 2,6-diisopropylphenyl, biphenyl, naphthyl, benzyl, pyridyl, furyl, quinolyl, morpholinyl, trimethylsilyl, dimethyl-t-butylsilyl, triphenylsilyl, triethoxysilyl, dimethylboryl, diphenylboryl, diphenoxyboryl, 1,2-dioxyphenylboryl, 2,2'-biphenoxyboryl, 2,2'-dinaphthoxyboryl, diphenylphosphino, dibutylphosphino, dimethylphosphino, dicyclohexylphosphino, dicyclopentylphosphino and methylphenylphosphino. In those embodiments where $R^1$ and $R^2$ are joined together in a ring structure, the ring (including $R^1$, $R^2$, and N) has from 3 to 15 non-hydrogen atoms preferably between 5 and 10 non-hydrogen atoms, more preferably between 5 and 6 non-hydrogen atoms, as part of the backbone of the ring. Specific examples of $R^1$ and $R^2$ together are ethylene (giving a 3-membered ring), butylene (giving a 5-membered ring), bicyclooctyl, bicyclohexyl, 2,2'-biphenyl (giving a dibenzo fused 5-membered ring), 2,2'-binaphthyl (giving a dinaphtho fused 5-membered ring) and the like.

In one preferred embodiment, $R^1$ is a substituted or unsubstitued phenyl. In the case of the substituted phenyl, there are from 1–5 substituents on the phenyl ring, with each of the substituents independently selected from the group consisting of halide, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. Even more preferably, there are 1, 2 or 3 substituents on the substituted phenyl and the substituents are selected from the group consisting of chloro, fluoro, iodo, bromo, methyl, ethyl, propyl, butyl, pentyl, hexyl, cyclopropyl, cyclobutyl, cyclopentyl, cyclohexyl, cyclooctyl, phenyl, naphthyl, benzyl, trimethylsilyl and isomers thereof, where applicable. Here and throughout, "where applicable" is intended to mean that for those compounds in the list that have isomers, the isomers are included without having to list each one, which is a form over substance issue. For example, isopropyl, n-butyl, s-butyl, t-butyl are all included isomers.

Also, more specifically, $R^3$ is selected from a group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl and silyl. Specific examples of $R^3$ are methyl, ethyl, propyl, butyl, cyclopentyl, cylcohexyl, cyclooctyl, phenyl, naphthyl, benzyl, trimethylsilyl, and the like.

In other embodiments, when X is oxygen or sulfur and a is 1, $R^3$ is selected from the group consisting of alkyl, substituted alkyl, heterocycloalkyl, substituted heterocycloalkyl, aryl, substituted aryl, heteroaryl, substituted heteroaryl or silyl. In one embodiment, $R^3$ may be a substituted phenyl having from 1–5 substituents on the phenyl ring, with each of the substituents independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. More specifically, there are typically 1, 2 or 3 substituents on the substituted phenyl and the substituents are selected from the group consisting of chloro, fluoro, iodo, bromo, methyl, ethyl, propyl, butyl, cyclopentyl, cylcohexyl, cyclooctyl, phenyl, naphthyl, benzyl, trimethylsilyl and isomers thereof, where applicable.

Each of $Q^1$ and $Q^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, boryl, silyl, amino, phosphino, alkoxy, aryloxy, halogens, and combinations thereof. Specific examples of each of $Q^1$ and $Q^2$ are methyl, ethyl, propyl, butyl, phenyl, t-butyl, cyclohexyl, benzyl, acetyl, benzoyl, propionyl, pyridyl, morpholinyl, dimethylboryl, dibutylboryl, methylphenylboryl, diphenylboryl, trimethylsilyl, triphenylsilyl, dimethylphenylsilyl, dimethyl-t-butylsilyl, dimethylamino, diethylamino, methylphenylamino, benzylmethylamino, diphenylphosphino, dimethylphosphino, methylphenylphosphino, methoxy, phenoxy, benzyloxy, tetrahydropyranyl, chloro and bromo. Optionally, $Q^1$ and $Q^2$ are joined together in a ring structure. In those embodiments where $Q^1$ and $Q^2$ are joined together in a ring, the ring (including $Q^1$, $Q^2$ and the two carbon atoms in the backbone of the ligand) has from 4 to 15 non-hydrogen atoms in the backbone of the ring. Specific examples of ring are cyclohexene, cyclopentene, cyclobutene, cyclooctene, cyclopentadiene, naphthalene, anthracene, acridine, dihydrofuran, benzene, pyridine, oxazoline, furan, and thiophene. One form of this option is preferred, such that the ligands of this invention may be characterized by the general formula:

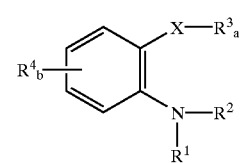

II wherein $R^1$, $R^2$, $R^3$, X and a each have the definition given above. In addition, $R^4$ is selected from the group consisting of electron withdrawing and electron donating groups and b is 0, 1, 2, 3 or 4. More specifically, of $R^4$ may be chosen from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, halogens and combinations thereof. Specific examples of $R^4$ include methyl, ethyl, propyl, butyl, pentyl, hexyl, phenyl, cyano, acetyl, benzoyl, nitro, dimethylamino, diethylamino, methylphenylamino, benzylmethylamino, trimethylsilyl, dimethylboryl, diphenylboryl, methylphenylboryl, dimethoxyboryl, chromium tricarbonyl, ruthenium tricarbonyl, cyclopentadienyl iron, and isomers thereof, where applicable. Optionally, two or more preferably four, $R^4$ groups combine to form a fused ring structure with the aromatic group that forms a part of the ligand backbone. The additional fused ring may or may not contain a heteroatom. Examples of the aromatic group that is part of the backbone as combined with two or more $R^4$ groups that have formed a fused ring are nathphalene, anthracene, quinoline, indole and the like.

Another embodiment is where the $R^1$ group is a substituted or unsubstituted phenyl, such that the ligands of this invention may be characterized by the general formula:

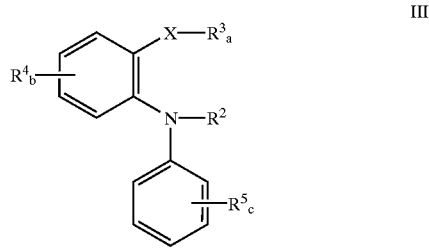

III wherein $R^2$, $R^3$, $R^4$, X, a and b each have the definition given above. In addition, $R^5$ is selected from the group consisting of electron withdrawing and electron donating groups and c is 0, 1, 2, 3, 4 or 5. More specifically, of $R^5$ may be chosen from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, halogens and combinations thereof. Specific examples of $R^5$ include methyl, ethyl, propyl, butyl, pentyl, hexyl, phenyl, cyano, acetyl, benzoyl, nitro, dimethylamino, diethylamino, methylphenylamino, benzylmethylamino, trimethylsilyl, dimethylboryl, diphenylboryl, methylphenylboryl, dimethoxyboryl, chromium tricarbonyl, ruthenium tricarbonyl, cyclopentadienyl iron and isomers thereof, where applicable. Optionally, two or more $R^5$ groups combine to form a fused ring structure with the aromatic group that forms a part of the ligand backbone. The additional fused ring may or may not contain a heteroatom. Examples of the aromatic group that is part of the backbone as combined with two or four $R^5$ groups that have formed a fused ring are nathphalene, quinoline, indole, anthracene and the like, either substituted or not.

The preferred ligands are synthesized using an aryl amination reaction. The synthesis can be carried out in solution phase or solid phase (using organic or inorganic supports). For solid-phase synthesis, the ligands may be left on the support and used with metal added metal complexes as heterogeneous catalysts. Alternatively, the ligands can be cleaved either before or after reaction with a metal precursor and then used as a homogeneous catalyst. One the general route for synthesis of the ligands of this invention is shown below in scheme 1:

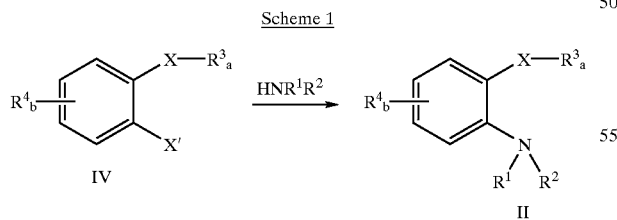

Scheme 1 where X' is a leaving group, such as a halogen, like Br, Cl, F or I or an aryl sulfonate, an alkyl sulfonate, triflate, nonaflate or another suitable leaving group. As shown in scheme 1, the synthesis employs an aryl amination reaction to attach the nitrogen group to the benzene ring at the appropriate location. The aryl amination reaction starts with a compound characterized by the general formula:

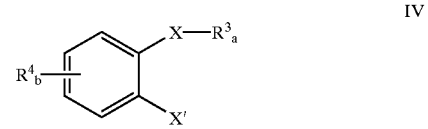

IV wherein $R^3$, $R^4$, X, a and b are as defined above and X' is selected from the group consisting of chloro, bromo, iodo, triflate, nonaflate, alkyl sulfonates, aryl sulfonates and tosylate. Starting compounds of this type can be purchased from Aldrich Chemical Company or prepared using known techniques. See, e.g., Greene, Theodora W. and Wuts, Peter G. M., Protecting Groups in Organic Synthesis, $2^{nd}$ Edition (John Wiley & Sons, New York, N.Y. 1991), herein incorporated by reference.

The aryl amination reaction uses an amine that can be characterized by the general formula $HNR^1R^2$, where $R^1$ and $R^2$ are as defined above. This aryl amination reaction is typically performed using a catalyst that comprises known or possibly new metal and ligand catalyst compositions. For example, the catalyst for the aryl amination reaction may be characterized by the general formula M'/L', where M' is a complex that contains a metal selected from the group consisting of late transition metals, preferably a Group 10 metal such as Pd, Ni or Pt. M' is any homogeneous or heterogeneous metal precursor catalyst or catalyst. L' is a ligand that may be selected from the group consisting of phosphine or nitrogen ligands. L' may be monodentate, bidentate, tridentate, hemi-labile, unsubstituted or substituted, supported or unsupported, water-soluble or insoluble, soluble or insoluble in organic solvents including fluorinated solvents. The reaction can take place at known conditions, such as a temperature of from room temperature to about 150° C. Aryl amination reactions are described in U.S. Pat. No. 5,576,460, herein incorporated by reference.

In some embodiments, it may be desirable to add a specific $R^2$ group. In this case, the ligands can be made by starting with $R^2$ as hydrogen and then adding a reactant to replace the hydrogen with the desired group in a reaction that may be characterized as shown below in Scheme 2:

Scheme 2

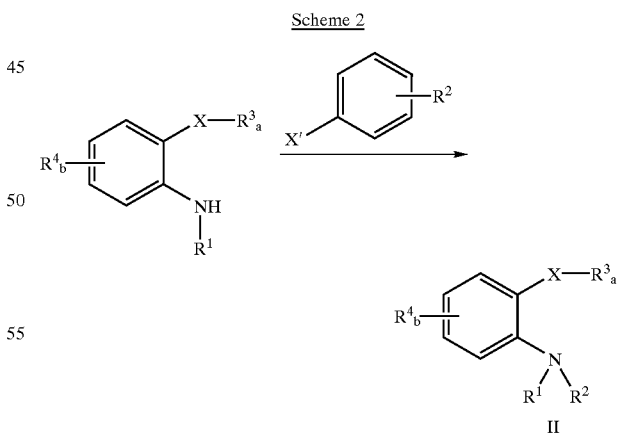

Once the desired ligand is formed, it may be combined with a metal atom, ion, compound or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ where M is a metal selected from the group consisting of Sc, Y and Groups 4, 5, 6, 7, 8, 9, 10, 11 and 12 of the Periodic Table of Elements. In more specific embodiments, M is selected from the group consisting of V, Ta, Ti, Zr, Zn Cr, W, Mo, Ru, Os, Co, Ni, Pd, Fe and Mn. n is a number 0, 1, 2, 3, 4 or 5. L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, cyclopentadienyl, substituted cyclopentadienyl, imido, oxo and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba=dibenzylideneacteone), $Pd(OAc)_2$ (Ac=acetate) and the like. In this context, the ligand to metal precursor compound ratio is in the range of about 0.01:1 to about 100:1, more preferably in the range of about 0.5:1 to about 20:1.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

In one form, the metal-ligand complexes may be characterized by one of the following general formulas:

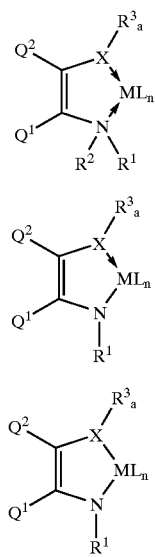

wherein each $R^1$, $R^2$, $R^3$, $Q^1$, $Q^2$ and X are as defined above; M is a transition metal selected from the group consisting of Sc, Y and Groups 4, 5, 6, 7, 8, 9, 10, 11 and 12 of the Periodic Table of Elements; L is independently each occurrence, a neutral and/or charged ligand; n is a number 0, 1, 2, 3, 4 or 5, depending on M and L; and a is 0, 1 or 2 depending on the element chosen for X and the type of bonding to M. For example, if X is oxygen or sulfur and the bonding is a dative bond (shown by the arrow), then a is 1. Similarly, if X is oxygen or sulfur and the bonding is a covalent bond, then a is 0. In other embodiments, X will be nitrogen that is datively bonded to M, meaning that a is 2. If X is nitrogen that is covalently bonded to M, then a is 1. In more specific embodiments, M is selected from the group consisting of V, Ta, Ti, Zr, Zn, Cr, W, Mo, Ru, Os, Co, Ni, Pd, Fe and Mn.

L is independently each occurrence, a neutral and/or charged ligand. Generally, L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, cyclopentadienyl, substituted cyclopentadienyl, imido, oxo and combinations thereof. When L is a charged ligand, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L is selected from the group consisting of arene, carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

n is the number 0, 1, 2, 3, 4 or 5. M can be neutral, cationic or anionic.

In yet another alternative form, the metal can bind only to the N atom. The various ligand embodiments can be rewritten in this form. For example, the metal complexes may be characterized by one of the general formulas:

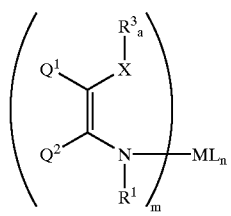

wherein each $R^1$, $R^3$, $R^4$, $Q^1$, $Q^2$, X, M, L, a, b and n are as defined above; and m is a number that is either 1, 2, 3 or 4.

When a preferred form of the ligand is employed, the metal complexes of this invention may be characterized by one of the following the general formulas:

IX
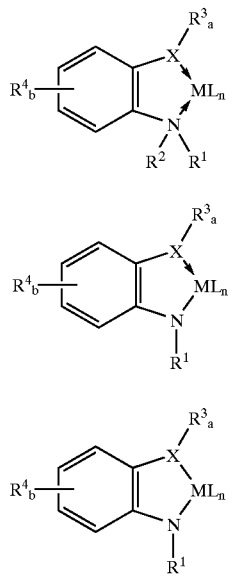

X

XI
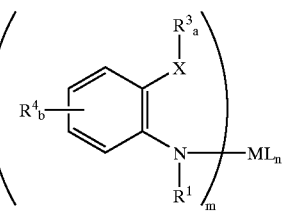

XII wherein each of $R^1$, $R^2$, $R^3$, $R^4$, M, L, X, a, b, m and n are as defined above.

When other preferred ligands are used, the metal complexes may be characterized by one of the following general formulas:

XIII
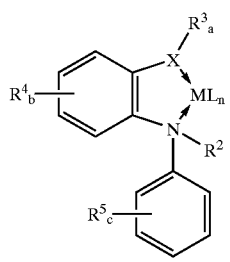

XIV
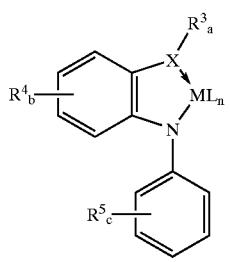

XV
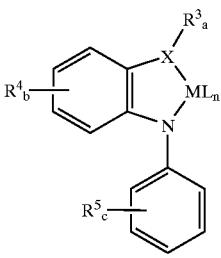

XVI
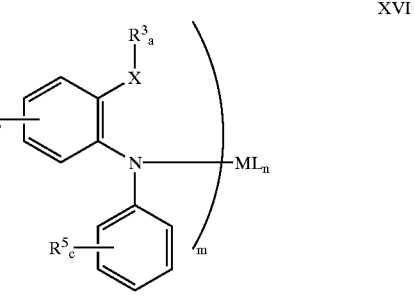

wherein each of $R^2$, $R^3$, $R^4$, $R^5$, M, L, X, a, b, c, m and n are as defined above.

The ligands of this invention bind to a metal via the N and X atoms, optionally via only the N atom, as explained above. Coordination modes described above may or may not depend on the nature of ligands L on the metal M, and for a given ancillary ligand of this invention the coordination modes may switch from one to another at different stages of a catalytic cycle.

These transition metal-ligand complexes catalyze reactions involving activation of and formation of bonds between H—Si, H—H, H—N, H—O, H—P, H—S, C—H, C—C, C=C, C≡C, C-halogen, C—N, C—O, C—S, C—P, and C—Si. Specifically, such reactions include carbonylation, hydroformylation, hydroxycarbonylation, hydrocarbonylation, hydroesterification, hydrogenation, hydrosilylation, hydroboration, hydroamination, epoxidation, aziridination, reductive amination, C—H activation, insertion, C—H activation-insertion, C—H activation-substitution, C-halogen activation, C-halogen activation-substitution, C-halogen activation-insertion, alkene metathesis, alkyne metathesis, polymerization, alkene oligomerization, alkene polymerization, alkyne oligomerization, alkyne polymerization, co-polymerization, CO-alkene co-oligomerization, CO-alkene co-polymerization, CO-alkyne co-oligomerization and CO-alkyne co-polymerization. These reactions may occur at previously known conditions (or possibly novel conditions). Moreover, these reactions may be homogeneous or heterogeneous. In the case of heterogeneous reactions, the ligands may be supported, with or without the metal coordinated, on an organic or inorganic support. Suitable supports include silicas, aluminas, zeolites, polyethyleneglycols, polystyrenes, polyesters, polyamides, peptides and the like.

Polymerization or oligomerization catalysis with the compositions and metal complexes of this invention is a particularly effective process. In particular, the complexes and compositions of this invention are active catalysts also for the polymerization of olefins, diolefins or acetylenically unsaturated compounds possibly in combination with an activator or activating technique. When an activator or activating technique is used, those of skill in the art may use alumoxanes, strong Lewis acids, compatible noninterfering activators and combinations of the foregoing. The foregoing activators have been taught for use with different metal complexes in the following references, which are hereby incorporated by reference in their entirety: U.S. Pat. Nos. 5,599,761, 5,616,664, 5,453,410, 5,153,157, 5,064,802, and EP-A-277,004. Preferred activators include methylalumoxane, trimethylaluminum, $AgBF_4$, $AgBPh_4$, $AgBAr'_4$, $NaBAr'_4$, $H(OEt_2)_2BAr'_4$ and the like (where Ar' is a substituted aromatic, like perfluorophenyl or $3,5\text{-}(CF_3)_2(C_6H_3)$). An example of a Lewis acid activator is $B(C_6F_5)_3$.

Ratios of neutral complex to activator are on the order of 1 to 1000 to 1000 to 1. A scavenger can also be used with this invention. Scavengers useful herein include metal complexes, alumoxanes, aluminum alkyls, Lewis acids and the like. Other additives that are standard for polymerization reactions can be used.

The catalysts herein may be used to polymerize ethylenically or acetylenically unsaturated monomers having from 2 to 20 carbon atoms either alone or in combination. Monomers include $C_2$ to $C_{20}$ α-olefins such as ethylene, propylene, 1-butene, 1-hexene, 1-octene, 4-methyl-1-pentene, styrene and mixtures thereof.

The compounds and catalysts of this invention usefully polymerize functionalized monomers, such as acetates and acrylates. Novel polymers, copolymers or interpolymers may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, foams, coatings, insulating devices and household items. Also, such functionalized polymers are useful as solid supports for organometallic or chemical synthesis processes.

Polymerization can be carried out in the Ziegler-Natta or Kaminsky-Sinn methodology, including temperatures of from 0° C. to 400° C. and pressures from atmospheric to 3000 atmospheres. In a preferred embodiment the process is a continuous process at a temperature of between –100° C. and 500° C. Suspension, solution, slurry, gas phase or high-pressure polymerization processes may be employed with the catalysts and compounds of this invention. Such processes can be run in a batch or continuous mode. Examples of such processes are well known in the art. A support for the catalyst may be employed, which may be alumina, silica or a polymers support. Methods for the preparation of supported catalysts are known in the art. Slurry, suspension, solution and high-pressure processes use a suitable solvent as known to those skilled in the art.

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. No. 5,776,359 generally discloses combinatorial methods and WO 98/03521 discloses combinatorial methods for organometallic chemistry, both of which are incorporated herein by reference. In this regard, the ligands, complexes or compositions may be prepared and/or tested in rapid serial and/or parallel fashion, e.g., in an array format. When prepared in an array format, for example, the ligands may be take the form of an array comprising a plurality of compounds wherein each compound can be characterized by either of the general formulas:

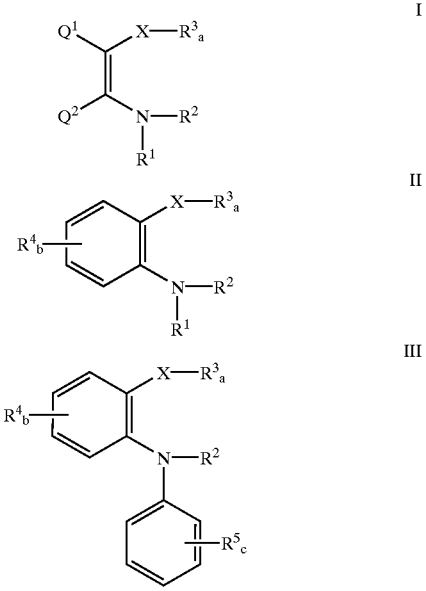

wherein each $R^1$, $R^2$, $R^3$, $R^4$, $R^5$, $Q^1$, $Q^2$, X, a, b and c is as defined above.

In such a combinatorial array, typically each of the plurality of compounds has a different composition and each compound is at a selected region on a substrate such that each compound is isolated from the other compounds. This isolation can take many forms, typically depending on the substrate used. If a flat substrate is used, there may simply be sufficient space between regions so that there cannot be interdiffusion between compounds. As another example, the substrate can be a microtiter or similar plate having wells so that each compound is in a region separated from other compounds in other regions by a physical barrier.

The array typically comprises at least 10 ligands, compounds, complexes or compositions each having a different chemical formula, meaning that there must be at least one different atom or bond differentiating the plurality in the array. In other embodiments, there are at least 25 compounds, complexes or compositions on or in the substrate each having a different chemical formula. In still other embodiments, there are at least 50 or 96 or 124 ligands, compounds, complexes or compositions on or in the substrate each having a different chemical formula. Because of the manner of forming combinatorial arrays, it may be that each compound, complex or composition is not pure. Typically, each compound in the plurality of compounds is at least 50% pure within its region. In other embodiments, each element of the array comprises the composition of matter described above, comprising the ligand and a metal precursor. The same array discussion above applies to arrays of this type. In still other embodiments, each element of the array is a metal-ligand complex defined above, including complexes V, VI, VII, VIII, IX, X, XI, XII, XIII, XIV, XV and XVI. The same array discussion above applies to arrays of this type.

The catalytic performance (activity and/or selectivity) of the ligands of this invention in combination with a suitable metal precursor, compositions of this invention or metal-ligand complexes of this invention can be tested in a combinatorial or high throughput fashion. For any of the listed transformations, thin layer chromatography (TLC) in combination with imaging technology may be employed. TLC is well known in the art, see for example Vol. 1,

*Thin-Layer Chromatography, Reagents & Detection Methods*, Jork et al. (VCH Publishers, New York, N.Y. 1990), incorporated herein by reference. Polymerizations or oligomerizations can also be performed in a combinatorial fashion, see, e.g., commonly owned provisional U.S. patent application Ser. No. 60/096,603, filed Aug. 13, 1998, herein incorporated by reference. High throughput screening can also be performed optically and in parallel, for example, as disclosed in commonly owned U.S. patent applications Ser. No. 09/067,448, filed Apr. 2, 1998, Ser. No. 08/947,085, filed Oct. 8, 1997, and Ser. No. 08/946,135, filed Oct. 7, 1997, each of which is incorporated by reference.

EXAMPLES

General: All reactions were performed under argon atmosphere in oven-dried glass Schlenk tubes using standard Schlenk techniques or in an inert atmosphere glove box. All aryl halides, all amines, sodium t-butoxide, bis (dibenzylideneacetone)palladium (Pd(dba)$_2$), benzene, ethanol, diethyl ether, methylene chloride, toluene, and 1,4-dioxane were purchased from commercial sources and used as received. All solvents used were of the anhydrous, Sure-seal® grade. Column chromatography was performed using commercially available Silica Gel 60 (particle size: 0.063–0.100 mm), hexanes and ethyl acetate. GCMS analyses were conducted on a Hewlett-Packard 5890 instrument. $^1$H, $^{13}$C, $^{31}$P NMR spectra were obtained using a Bruker 300 MHz FT-NMR spectrometer. Chemical shifts in $^1$H and $^{13}$C NMR spectra were calibrated with reference to the chemical shift of residual protiated solvent. Chemical shifts in $^{31}$P NMR spectra were calibrated with reference to 85% H$_3$PO$_4$; a negative value of chemical shift denotes resonance upfield from H$_3$PO$_4$.

Example 1

2-(Octylamino)anisole (1): A mixture of 2-chloro-anisole (0.12 mL, 0.94 mmol), octylamine (0.19 mL, 1.14 mmol), NaO$^t$Bu (125 mg, 1.30 mmol), Pd(dba)$_2$ (12 mg, 0.02 mmol), Ligand 1 (22 mg, 0.06 mmol) in toluene (4 mL) at 105° C. for 3 hours and analyzed by GCMS. Ligand 1 was made in accord with the procedure disclosed in commonly assigned provisional U.S. patent application Ser. No. 60/095,612, filed Aug. 8, 1998, incorporated herein by reference. The reaction was cooled to room temperature, taken up in diethyl ether (125 mL), washed with water (30 mL) and brine (30 mL), dried over MgSO$_4$, filtered and concentrated in vacuo. The crude product was purified by column chromatography on silica gel using hexanes as the eluent to afford the title compound, whose structure is shown below as compound (1), after drying under vacuum, as an colorless oil (yield: 230 mg, 95%).

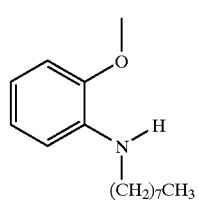

(1)

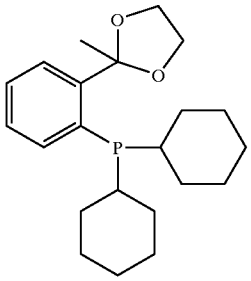

Ligand 1

Analysis for the compound showed: $^1$H NMR (CDCl$_3$): δ 6.92 (t, J=7.6 Hz, 1H, ArH), 6.81 (d, J=7.6Hz, 1H, ArH), 6.71 (d, J=7.6Hz, 1H, ArH), 6.67 (t, J=7.6Hz, 1H, ArH), 4.22 (br., 1H,—NH), 3.86 (s, 3H, —OCH$_3$), 3.16 (t, J=7.2 Hz, 2H, —NCH$_2$—), 1.69 (pentet, 2H, —NCH$_2$CH$_2$CH$_2$_), 1.35 (br., 10H, 5—CH$_2$—'s), 0.95 (br., 3H, CH$_3$). $^{13}$C NMR (CDCl$_3$): δ 146.7, 138.5, 121.3, 115.9, 109.7, 109.3, 55.3, 43.7, 31.8, 29.5, 29.4, 29.2, 27.2, 22.6, 14.0.

Example 2

2-(2,6-Diisopropylanilino)anisole (2): The title compound, with the structure shown below, (439 mg, 97% yield) was obtained as a colorless oil from the reaction of 2-bromoanisole (300 mg, 1.60 mmol), 2,6-diisopropylaniline (298 mg, 1.68 mmol), NaO$^t$Bu (161 mg, 1.68 mmol), Pd(dba)$_2$ (18 mg, 0.03 mmol), Ligand 2 (30 mg, 0.08 mmol) in toluene (4 mL) at 105° C. for 1 hour. Work up for the compound was as in Example 1. Ligand 2 was made in accord with the, procedure disclosed in commonly assigned U.S. patent application Ser. No. 09/062,128, filed Apr. 17, 1998, herein incorporated by reference. Ligand 2 has the following structure:

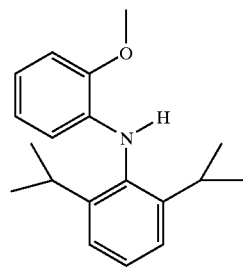

(2)

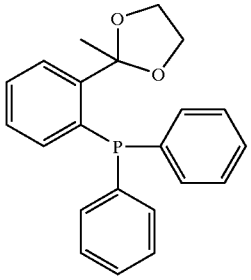

Ligand 2

Analysis for the title compound showed: $^1$H NMR (CDCl$_3$): δ 7.41–7.21 (m, 3H, ArH), 6.94 (d, 1H, J=7.4 Hz, ArH), 6.83–6.73 (m, 2H, ArH), 6.23 (d, 1H, J=7.4 Hz, ArH), 5.72 (br., 1H, NH), 4.01 (s, 3H, OMe), 3.28 (heptet, 2H, J=6.9 Hz, 2 CHMe$_2$'s), 1.25 (d, 12H, J=6.9 Hz, 2 Me$_2$'s). $^{13}$C NMR (CDCl$_3$): δ 147.6, 146.2, 137.9, 135.4, 127.0, 123.7, 121.1, 116.7, 110.9, 109.7, 55.7, 28.1, 23.9. Anal. for $C_{19}H_{25}NO$; Calcd: C, 80.52; H, 8.89; N, 4.94; Found: C, 79.93; H, 8.89; N, 4.85.

Example 3

$(2,6\text{-}(i\text{-Pr})_2C_6H_3)N(2\text{-MeOC}_6H_4))Ni(C_6H_5)(PPh_3)$ (3): trans-$Ni(PPh_3)_2(Ph)(Cl)$ (241 mg, 0.35 mmol) was suspended in 5 mL $Et_2O$ and the suspension was cooled to −35C. $(2,6\text{-}(i\text{-Pr})_2C_6H_3)(2\text{-MeOC}_6H_4)NLi$ (102 mg, 0.36 mmol) was dissolved in 2 mL $Et_2O$, the solution was cooled to −35° C. and then added to the cooled suspension of trans-$Ni(PPh_3)_2(Ph)(Cl)$. The reaction was allowed to warm to room temperature and was stirred for 3 hours. A greenish-grey precipitate formed. The precipitate was collected, washed with $Et_2O$ (10 mL) and dried (yield=148 mg; 60%). The complex has the following expected structure:

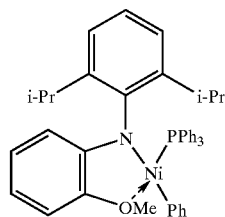

(3)

Analysis for the complex showed: $^1H$ NMR ($C_6D_6$) δ 6.2–7.7 (m, 27H, Ar), 4.21 (sept, 2H, CHMe$_2$), 2.83 (s, 3H, OMe), 1.30 (overlapping doublets, 12H, CHMe$_2$)

Example 4

$(2,4,6\text{-}(i\text{-Pr})_3C_6H_2)N(2\text{-PhOC}_6H_4))Ni(C_6H_5)(PPh_3)$ (4): trans-$Ni(PPh_3)_2(Ph)(Cl)$ (255 mg, 0.37 mmol) was suspended in 5 mL $Et_2O$ and the suspension was cooled to −35C. $(2,4,6\text{-}(i\text{-Pr})_3C_6H_2)(2\text{-PhOC}_6H_4)NLi$ (140 mg, 0.36 mmol) was dissolved in 2 mL $Et_2O$, the solution was cooled to −35C and then added to the cooled suspension of trans-$Ni(PPh_3)_2(Ph)(Cl)$. The reaction was allowed to warm to room temperature and was stirred for 3 hours. Solvent was removed in vacuo and the resulting red-brown solid was washed with hexane (10 mL) and dried (yield=142 mg, 51%). The complex has the following expected structure:

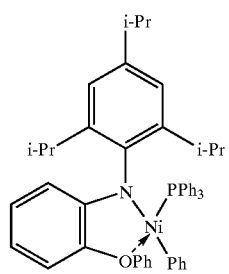

(4)

Analysis for the complex showed: $^1H$ NMR ($C_6D_6$) δ 6.0–7.2 (m, 31H, Ar), 4.25 (sept, 2H, ortho-CHMe$_2$), 2.91 (sept, 1H, para-CHMe$_2$), 1.42 (d, 6H, para-CHMe$_2$), 1.32 (overlapping doublets, 12H, ortho-CHMe$_2$).

Example 5

This example uses the complex of Example 3 with an activator to oligomerize ethylene. Complex (3) from Example 3 (24 mg, 0.035 mmol) and $B(C_6F_5)_3$ (40 mg, 0.078 mmol) were combined in a thick-walled glass flask fitted with a teflon valve. 5.0 mL toluene was added and the mixture was stirred for 5 minutes. The mixture was placed under constant ethylene pressure (25 psi) and stirred for 1.5 hours. An aliquot of the reaction mixture was analyzed by $^1H$ NMR spectroscopy and the yield of oligomers was calculated by comparison of the integrals of the peaks associated with the ethylene. oligomers to the integral of the toluene methyl peak (yield=47 mmol oligomers; 900 TO/hour).

Example 6

This example uses the complex of Example 4 with an activator to oligomerize ethylene. Complex (4) from Example 4 (27 mg, 0.035 mmol) and $B(C_6F_5)_3$ (70 mg, 0.136 mmol) were combined in a thick-walled glass flask fitted with a teflon valve. 5.0 mL toluene was added and the mixture was stirred for 5 minutes. The mixture was placed under ethylene (15 psi) and stirred for 15 minutes. An aliquot of the reaction mixture was analyzed by $^1H$ NMR spectroscopy and the yield of oligomers was calculated by comparison of the integrals of the peaks associated with the ethylene oligomers to the integral of the toluene methyl peak (yield=16.3 mmol oligomers; 1860 TO/hour).

Example 7

1-(tert-Butyldimethylsiloxy)-2-mesitylaminobenzene (5): The starting compound 1-bromo-2-(tert-butyldimethylsiloxy)benzene was first synthesized from the reaction of 2-bromophenol (9.58 g, 113 mmol) and t-butyldimethylsilylchloride (17.16 g, 114 mmol) in $CH_2Cl_2$ (about 100 mL) in the presence of imidazole (13.62 g, 200 mmol) at room temperature for 16 hours (yield 96%). See, T. W. Greene et al., supra for general details on this reaction. Subsequently, a mixture of 1-bromo-2-(tert-butyldimethylsiloxy)benzene (as synthesized above) (2.87 g, 10.0 mmol), 2,4,6-trimethylaniline (1.35 g, 10.0 mmol), sodium tert-butoxide (1.15 g, 12.0 mmol), $Pd(dba)_2$ (29 mg, 50 μmol) and Ligand 2 (shown above in Example 2) (35 mg, 100 μmol) in 40 mL toluene was heated to 100° C. for 20 hr. The reaction was worked up by aqueous quenching and extraction with ether. The crude product was purified by flash chromatography on a silica gel column, affording 2.70 g of the desired material as a colorless oil (79%). The compound (5) has the following structure:

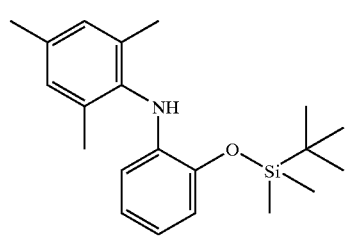

(5)

Analysis for the compound showed: $^1H$-NMR ($CDCl_3$, 300 MHz) δ 0.26 (s, 6H), 1.02 (s, 9H), 2.14 (s, 6H), 2.29 (s, 3H), 5.45 (brs, 1H), 6.09 (dd, J=1.5, 7.8, 1H), 6.56 (dt, J=1.5, 7.7, 1H), 6.69 (dt, J=1.5, 7.7, 1H), 6.77 (dd, J=1.2, 7.5, 1H), 6.97 (s, 2H). MS (EI+) 341 (M+), 284 (bp).

Example 8

1-Mesitylamino-2-phenoxy-benzene (6): A mixture of 2-bromomesitylene (1.99 g, 10.0 mmol), 2-phenoxyaniline (1.85 g, 10.0 mmol), sodium tert-butoxide (1.15 g, 12.0 mmol), $Pd(dba)_2$ (58 mg, 100 μmol) and Ligand 2 (shown above in Example 2) (70 mg, 200 μmol) in 50 mL toluene was heated to 100° C. for 6 days. The reaction was worked up by aqueous quenching and extraction with ether. The crude product was purified by flash chromatography on a silica gel column, affording 2.94 g of the desired material as a slightly yellow oil (97%). The compound (6) has the following structure:

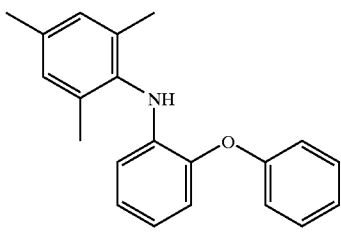
(6)

Analysis for the compound showed: $^1$H-NMR (CDCl$_3$, 300 MHz) δ 2.10 (s, 6H), 2.34 (s, 3H), 5.44 (brs, 1H), 6.22 (dd, J=1.5, 8.0, 1H), 6.87–6.75 (m, 4H), 7.01–7.07 (m, 3H), 7.31 (t, J=7.8, 2H). MS (EI+) 303 (M+).

Example 9

1-Phenoxy-2-(2,4,6-triisopropylphenoxy)benzene (7): A mixture of 2-bromo-1,3,5-triisopropylbenzene (2.83 g, 10.0 mmol), 2-phenoxyaniline (1.85 g, 10.0 mmol), sodium tert-butoxide (1.15 g, 12.0 mmol), Pd(dba)$_2$ (58 mg, 100 µmol) and Ligand 2 (shown above in Example 2) (70 mg, 200 µmol) in 50 mL toluene was heated to 100° C. for 18 hr. The reaction was worked up by aqueous quenching and extraction with ether. The crude product was purified by flash chromatography on a silica gel column, affording 3.38 g of the desired material as a slightly yellow solid (87%). The compound (7) has the following structure:

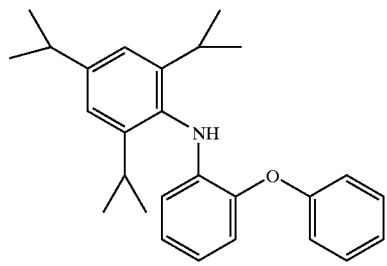
(7)

Analysis for the compound showed: $^1$H-NMR (CDCl$_3$, 300 MHz) δ 1.06 (d, J=6.8, 12H), 1.25 (d, J=6.9, 6H), 2.88 (sep, J=6.9, 1H), 3.05 (sep, J=6.9, 2H), 5.34 (brs, 1H), 6.24 (dd, J=1.3, 8.0, 1H), 6.63 (dt, J=1.4, 7.8, 1H), 6.89 (dt, J=1.1, 7.9, 1H), 7.01–7.07 (m, 3H), 7.31 (dt, J=2.1, 8.6, 2H). MS (EI+) 387 (M+).

Example 10

This is an example of making a ligand on a solid support, in this case a resin bead having a tether. The tether, 2-(3-bromo-4-methoxyphenyl)ethanol, was first synthesized as follows: To 3-bromo-4-methoxyphenylacetic acid (12.26 g, 50.0 mmol) in 100 mL tetrahydrofuran (THF) was added borane dimethylsulfide complex (6.0 mL, 60.0 mmol) with cooling in an ice bath. The reaction was stirred at room temperature overnight. The reaction mixture was concentrated in vacuuo. The residue was taken up in 100 mL methanol and concentrated in vacuuo to remove borate. Thie operation was repeated three times, affording analytically pure alcohol as a yellow oil (10.86 g, 94% yield). See N. M. Yoon, et al., *J. Org. Chem.*, 38, 2786 (1973), herein incorporated by reference. Then, 2-(3-Bromo-4-methoxyphenyl) ethanol was immobilized onto Wang resin (100–200 mesh, 0.89 mmol/g loading) according to the procedure described by Hanessian and Xie (Tetrahedron Letters, 39, 1998, 733–736), herein incorporated by reference. The resulting resin (1.50 g, 1.14 mmol), 2,6-diisopropylaniline (404 mg, 2.28 mmol), sodium tert-butoxide (219 mg, 2.28 mmol), Pd(dba)$_2$ (13 mg, 23 µmol) and Ligand 2 (shown above in Example 2) (16 mg, 46 µmol) in 10 mL toluene were heated to 100° C. for 23 hr. The resin was drained, washed with three times with 10 mL of toluene (referred to as "10 mL×3"), and then 10 mL×5 THF, 10 mL×3 DMF, 10 mL×3H2O, 10 mL×3 methanol, 10 mL×3 DMF, 10 mL×3 THF, and 10 mL CH$_2$Cl$_2$, and dried under vacuum, affording 1.61 g of tan color resin (100% based on the loading of the Wang resin). In order to characterize the resin, 144 mg of the resin was treated with 10 [v/v]% trifluoroacetic acid in CH$_2$Cl$_2$ for 30 min. at 21° C. The resin was filtered off and rinsed with 1 mL×5 CH$_2$Cl$_2$. The combined filtrates were washed with sat. aqueous NaHCO$_3$, dried over Na$_2$SO$_4$, filtered and concentrated, affording 24.9 mg of a brown oil. The GC-MS analysis of the cleaved product revealed a mixture of the desired coupling product (70%) and its trifluoroacetic acid ester (30%) that was presumably formed during the acid cleavage, and it did not show unreacted 2-(3-bromo-4-methoxyphenyl)ethanol. The resin bound ligand is shown below as structure (8), and the cleaving reaction shows the unbound ligand as structure 9:

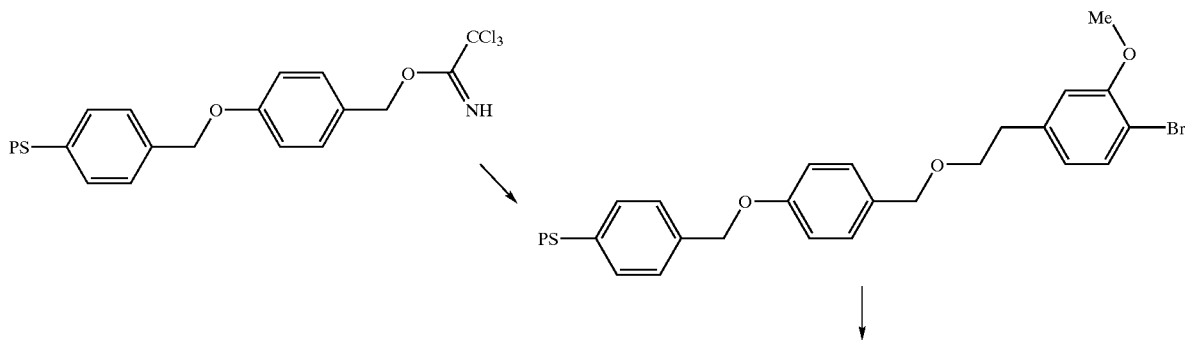

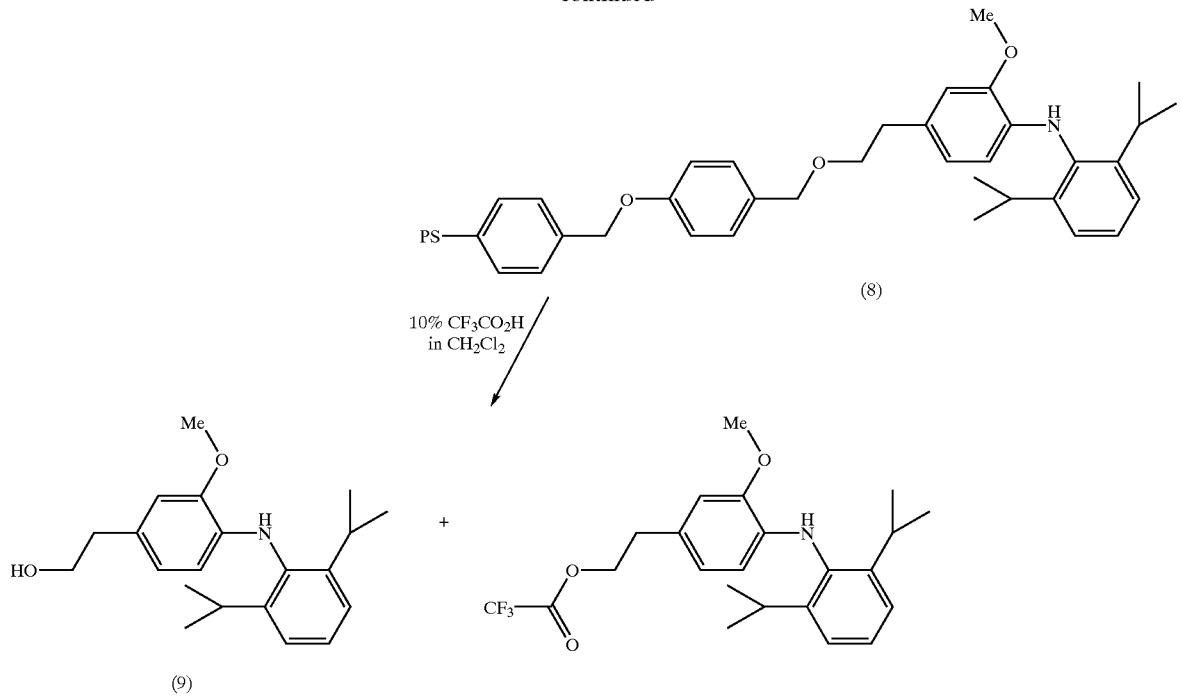

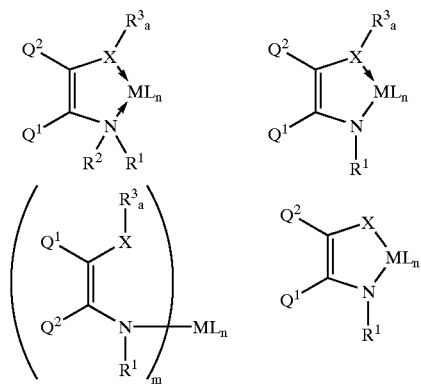

Analysis of the cleaved product (9) showed: $^1$H-NMR (CDCl$_3$, 300 MHz) δ 1.13 (d, J=6.9, 6H), 2.61 (t, J=6.6, 2H), 3.14 (sep, J=6.6, 2H), 3.66 (t, J=6.5, 2H), 3.94 (s, 3H), 5.62 (brs, 1H), 5.95 (d, J=2.1, 1H), 6.51 (dd, J=2.1, 8.1, 1H), 6.79 (d, J=8.1, 1H), 6.89 (dt, J=1.1, 7.9, 1H), 7.20–7.32 (m, 4H). MS (EI+) 327 (M+).

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A complex characterized by one of the following general formulas:

wherein each R$^1$, R$^2$ and R$^3$ is independently selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, R$^1$ and R$^2$ are joined together in a ring structure;

Q$^1$ and Q$^2$ are, independently, selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, Q$^1$ and Q$^2$ are joined together in a ring structure;

X is selected from the group consisting of oxygen and sulfur; a is 0 or 1;

M is a transition metal selected from the group consisting of Sc, Y and Groups 4, 5, 8, 9, 11 and 12 of the Periodic Table of Elements;

L is independently each occurrence, a ligand;

n is a number 0, 1, 2, 3, 4 or 5; and m is 1, 2, 3 or 4.

2. The complex of claim 1, wherein M is selected from the group consisting of Sc, Y, Zr, Ti, Hf, V, Nb, Ta, Zn, Fe, Ru, Os, Co and Rh.

3. The complex of claim 2, wherein M is selected from the group consisting of Co, Fe, Ru, Rh and V.

4. The complex of claim 1, wherein L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, cyclopentadienyl, substituted cyclopentadienyl, imido, oxo and combinations thereof.

5. The complex of claim 1, wherein L is selected from the group consisting of alkene, diene, carbon monoxide, isocyanide, nitrous oxide, PA₃, NA₃, OA₂, SA₂, SeA₂, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

6. The complex of claim 1, wherein $R^1$ is a substituted or unsubstitued phenyl.

7. The complex of claim 6, wherein $R^1$ is a substituted phenyl and there are from 1–5 substituents on said phenyl ring, with each of said substituents independently selected from the group consisting of halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof.

8. The complex of claim 7, wherein there are 1, 2 or 3 substituents on said substituted phenyl and said substituents are selected from the group consisting of chloro, fluoro, iodo, bromo, methyl, ethyl, propyl, butyl, cyclopentyl, cyclohexyl, cyclooctyl, phenyl, naphthyl, benzyl, trimethylsilyl and isomers thereof.

9. The complex of claim 1, wherein X is oxygen, a is 1 and $R^3$ is selected from the group consisting of alkyl, substituted alkyl, aryl, substituted aryl or silyl.

10. The complex of claim 9, wherein $R^3$ is a substituted phenyl and there are from 1–5 substituents on said phenyl ring, with each of said substituents independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof.

11. The complex of claim 1, wherein $Q^1$ and $Q^2$ are joined together in a ring structure with the backbone of the compound, such that the compound can be characterized by one of the following general formulas:

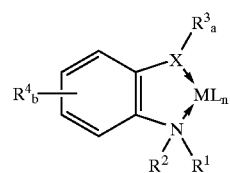

IX

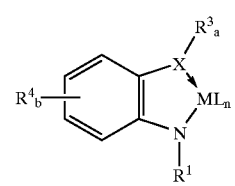

X

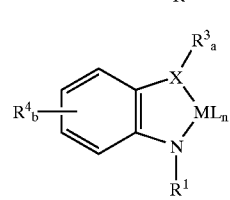

XI

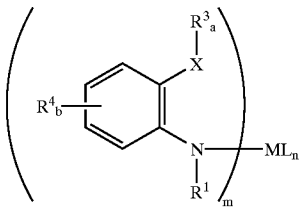

XII wherein $R^1$, $R^2$, $R^3$, X, M, L, n, m and a each have the definition given above; $R^4$ is selected from the group consisting of electron withdrawing and electron donating groups; and b is 0, 1, 2, 3 or 4.

12. The complex of claim 11, wherein $R^4$ is selected from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, halogens and combinations thereof.

13. The complex of claim 12, wherein b is 1, 2 or 3 and $R^4$ is selected from the group consisting of methyl, ethyl, propyl, butyl, pentyl, phenyl, cyano, acetyl, benzoyl, nitro, dimethylamino, diethylamino, methylphenylamino, benzylmethylamino, trimethylsilyl, dimethylboryl, diphenylboryl, methylphenylboryl, dimethoxyboryl, chromium tricarbonyl, ruthenium tricarbonyl, cyclopentadienyl iron and isomers thereof where applicable.

14. The complex of claim 13, wherein two or more $R^4$ groups combine to form a fused ring structure with the aromatic group that forms a part of the ligand backbone.

15. The complex of claim 14, wherein the aromatic group that is part of the backbone as combined with two or more $R^4$ groups that have formed a fused ring are substituted or unsubstituted nathphalene, substituted or unsubstituted quinoline or substituted or unsubstituted indole.

16. The complex of claim 11, wherein $R^1$ is a substituted or unsubstituted phenyl such that the compound can be characterized by one of the following general formulas:

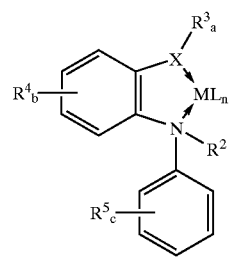

XIII

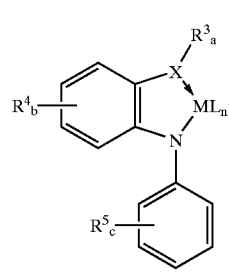

XIV

-continued

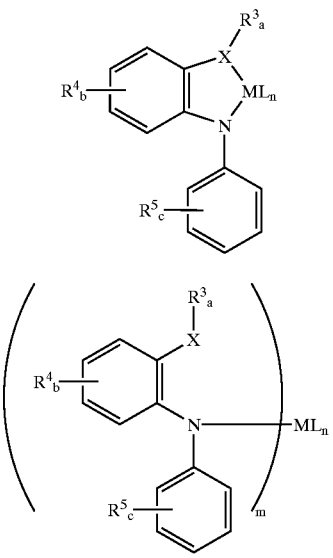

wherein $R^2$, $R^3$, $R^4$, X, M, L, n, m, a and b each have the definition given above, $R^5$ is selected from the group consisting of electron withdrawing and electron donating groups; and c is 0, 1, 2, 3, 4 or 5.

17. The complex of claim 16, wherein $R^5$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, halogens and combinations thereof.

18. A composition of matter comprising:
(a) a compound characterized by the general formula:

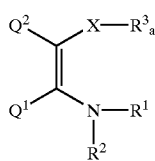

wherein each $R^1$, $R^2$ and $R^3$ is independently selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure;
$Q^1$ and $Q^2$ are, independently, selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof, optionally, $Q^1$ and $Q^2$ are joined together in a ring structure;
X is selected from the group consisting of oxygen or sulfur; and a is 0 or 1, and
(b) a metal precursor characterized by the general formula $M(L)_n$, where M is a transition metal selected from the group consisting of Sc, Y and Groups 4, 5, 8, 9, 11 and 12 of the Periodic Table of Elements; L is independently each occurrence, a ligand; and n is a number 0, 1, 2, 3, 4 or 5.

19. The composition of claim 18 wherein the ratio of compound to metal precursor is in the range of about 0.01:1 to about 100:1.

20. The composition of claim 19, wherein the ratio of compound to metal precursor is in the range of about 0.5:1 to about 20:1.

21. The composition of claim 18, wherein $Q^1$ and $Q^2$ are joined together in a ring structure with the backbone of the compound, such that the compound can be characterized by the general formula:

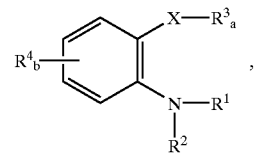

wherein $R^1$, $R^2$, $R^3$, X and a each have the definition given in claim 18; $R^4$ is selcted from the group consisting of electron withdrawing an electron donating groups; and b is 0, 1, 2, 3 or 4.

22. The composition of claim 21, wherein $R^1$ is a substituted or unsubstituted phenyl such that the compound can be characterized by the general formula:

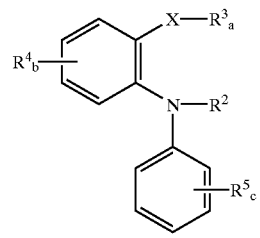

wherein $R^2$, $R^3$, X, and a each have the definition given in claim 18, $R^4$ and b each have the definition given in claim 21, each $R^5$ is selected from the group consisting of electron withdrawing and electron donating groups; and c is 0, 1, 2, 3, 4 or 5.

23. The complex of claim 1 wherein M is selected from the group consisting of Sc, Y, Ti, Zr and Hf.

24. The complex of claim 1 wherein M is Hf or Zr.

25. The composition of claim 18, wherein M selected from the group consisting of Sc, Y, Ti, Hf and Zr.

26. The complex of claim 1 wherein the complex is characterized by the general formula:

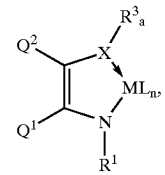

and wherein M is selected from the group consisting of Sc, Y, Ti, Hf and Zr and $Q^1$, $Q^2$, X, L, $R^1$, $R^3$, n and a are as defined in claim 1.

27. The complex of claim 26 wherein $R^1$ and $R^3$ are independently selected from the group consisting of aryl, substituted aryl, alkyl and substituted alkyl.

28. The complex of claim 26 wherein $R^1$ and $R^3$ are independently selected from the group consisting of substituted and unsubstituted phenyl.

29. The complex of claim 26 wherein $R^1$ and $R^3$ are independently selected from the group consisting of methyl, ethyl, propyl, butyl, cyclohexyl, cyclopropyl, cycloheptyl, t-butyl, phenyl, 2,4,6-trimethylphenyl, 2,4,6-triisopropylphenyl, 2,6-dimethylphenyl, 2,6-diisopropylphenyl, biphenyl, naphthyl, benzyl, pyridyl, furyl, quinolyl, morpholinyl, trimethylsilyl, dimethyl-t-butylsilyl, triphenylsilyl, triethoxysilyl, dimethylboryl, diphenylboryl, diphenoxyboryl, 1,2-dioxyphenylboryl, 2,2'-biphenoxyboryl, 2,2'-dinaphthoxyboryl, diphenylphosphino, dibutylphosphino, dimethylphosphino, dicyclohexylphosphino, dicyclopentylphosphino and methylphenylphosphino.

30. The complex of claim 26 wherein $R^1$ is a substituted phenyl having from 1–5 substituents on the phenyl ring, with each of the substituents independently selected from the group consisting of halide, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof.

31. The complex of claim 30 wherein there are 1, 2 or 3 substituents on the substituted phenyl and the substituents are selected from the group consisting of chloro, fluoro, iodo, bromo, methyl, ethyl, propyl, butyl, pentyl, hexyl, cyclopropyl, cyclobutyl, cyclopentyl, cyclohexyl, cyclooctyl, phenyl, naphthyl, benzyl, trimethylsilyl and isomers thereof.

32. The complex of claim 1 wherein the complex is characterized by the general formula:

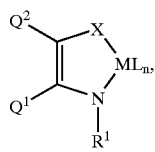

and wherein M is selected from the group consisting of Sc, Y, Ti, Hf and Zr and $Q^1$, $Q^2$, X, L, $R^1$, $R^3$, n and a are as defined in claim 1.

33. The complex of claim 31 wherein $R^1$ is selected from the group consisting of aryl, substituted aryl, alkyl and substituted alkyl.

34. The complex of claim 32 wherein $R^1$ is selected from the group consisting of substituted and unsubstituted phenyl.

35. The complex of claim 32 wherein $R^1$ is selected from the group consisting of methyl, ethyl, propyl, butyl, cyclohexyl, cyclopropyl, cycloheptyl, t-butyl, phenyl, 2,4,6-trimethylphenyl, 2,4,6-triisopropylphenyl, 2,6-dimethylphenyl, 2,6-diisopropylphenyl, biphenyl, naphthyl, benzyl, pyridyl, furyl, quinolyl, morpholinyl, trimethylsilyl, dimethyl-t-butylsilyl, triphenylsilyl, triethoxysilyl, dimethylboryl, diphenylboryl, diphenoxyboryl, 1,2-dioxyphenylboryl, 2,2'-biphenoxyboryl, 2,2'-dinaphthoxyboryl, diphenylphosphino, dibutylphosphino, dimethylphosphino, dicyclohexylphosphino, dicyclopentylphosphino and methylphenylphosphino.

36. The complex of claim 32 wherein $R^1$ is a substituted phenyl having from 1–5 substituents on the phenyl ring, with each of the substituents independently selected from the group consisting of halide, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof.

37. The complex of claim 36 wherein there are 1, 2 or 3 substituents on the substituted phenyl and the substituents are selected from the group consisting of chloro, fluoro, iodo, bromo, methyl, ethyl, propyl, butyl, pentyl, hexyl, cyclopropyl, cyclobutyl, cyclopentyl, cyclohexyl, cyclooctyl, phenyl, naphthyl, benzyl, trimethylsilyl and isomers thereof.

* * * * *